US012697299B2

(12) United States Patent
Brown

(10) Patent No.: US 12,697,299 B2
(45) Date of Patent: Aug. 4, 2026

(54) MAXIMIZING DISTRIBUTION AND MINIMIZING WASHOUT OF INJECTATES IN BONE AND METHOD FOR ENHANCED ASPIRATE EXTRACTION

(71) Applicant: YALE UNIVERSITY, New Haven, CT (US)

(72) Inventor: Elliot Brown, Barrington, RI (US)

(73) Assignee: YALE UNIVERSITY, New Haven, CT (US)

( * ) Notice: Subject to any disclaimer, the term of this patent is extended or adjusted under 35 U.S.C. 154(b) by 1150 days.

(21) Appl. No.: 17/609,222

(22) PCT Filed: May 7, 2020

(86) PCT No.: PCT/US2020/031919
§ 371 (c)(1),
(2) Date: Nov. 5, 2021

(87) PCT Pub. No.: WO2020/227558
PCT Pub. Date: Nov. 12, 2020

(65) Prior Publication Data
US 2022/0211645 A1      Jul. 7, 2022

Related U.S. Application Data

(60) Provisional application No. 62/844,592, filed on May 7, 2019.

(51) Int. Cl.
*A61K 9/00* (2006.01)
*A61K 31/137* (2006.01)
*A61K 45/06* (2006.01)

(52) U.S. Cl.
CPC .......... *A61K 9/0019* (2013.01); *A61K 31/137* (2013.01); *A61K 45/06* (2013.01); *A61M 2210/02* (2013.01)

(58) Field of Classification Search
CPC .......... A61M 5/46; A61M 5/48; A61M 5/484; A61M 2205/3331; A61M 2205/3334;
(Continued)

(56) References Cited

U.S. PATENT DOCUMENTS 8,568,355 B2    10/2013  Min
2005/0287134 A1*  12/2005  Klein ................... A61K 9/0021
514/649
(Continued)

FOREIGN PATENT DOCUMENTS

EP          1733684        12/2006

OTHER PUBLICATIONS

De Bruyn, Peter et al., The Migration of Blood Cells of the Bone Marrow through the Sinusoidal Wall, 1971 (Year: 1971).*
(Continued)

*Primary Examiner* — Kami A Bosworth
*Assistant Examiner* — Avery Smale
(74) *Attorney, Agent, or Firm* — Riverside Law LLP

(57) ABSTRACT

The present invention provides methods of distributing agents into bone and the maintenance of those agents within bone. These methods include mechanical, rheological, pharmacological, and other methods. By maintaining injectates within a targeted location in bone and increasing their distribution in bone, the methods are useful for purposes including but not limited to increasing local concentration, improving therapeutic effectiveness, increasing duration of action, and decreasing systemic toxicity. These same methods can displace the contents of bone toward a harvesting instrument for purposes of collection with similar and complimentary methods. The methods are useful for controlling the rate of egress of intraosseous distribution of agents or cells for a variety of purposes, including but not limited to: augmenting stem cell recovery in bone marrow aspiration,
(Continued)

Therapeutic Dosing
Infusion needle
Aspiration needle
Harvesting or pressure equilibration
Dosed portion
Vasoconstriction Dosing
Iliac Crest
Draining veins
Vasoconstriction Dosing
X-ray showing flow through bone chemotherapy, medication delivery, treatment of infection, bone augmentation, and the like.

9 Claims, 12 Drawing Sheets

(58) Field of Classification Search
CPC ...... A61M 2205/3344; A61M 2210/02; A61M 5/1582; A61M 2202/0482; A61K 31/137; A61K 9/0019; A61K 45/06
See application file for complete search history.

(56) References Cited

U.S. PATENT DOCUMENTS

| | | | |
|---|---|---|---|
| 2007/0198043 A1 | 8/2007 | Cox | |
| 2009/0318882 A1* | 12/2009 | Adler | ..................... A61C 19/06 |
| | | | 514/448 |
| 2013/0243864 A1* | 9/2013 | Macdonald | .......... A61K 9/0019 |
| | | | 424/490 |
| 2013/0324910 A1 | 12/2013 | Ohri | |
| 2018/0000465 A1* | 1/2018 | Brown | ................. A61B 10/025 |
| 2018/0116693 A1* | 5/2018 | Blanchard | ............. A61M 5/158 |
| 2018/0280613 A1 | 10/2018 | Skelton | |
| 2018/0344298 A1 | 12/2018 | Schenden | |

OTHER PUBLICATIONS

Extended European Search Report issued in App. No. EP20802623. 7, dated Apr. 28, 2023, 30 pages.
Ito et al., "Anesthetic duration of lidocaine with 10% dextran is comparable to lidocaine with 1:160 000 epinephrine after intraosseous injection in the rabbit", Oral Surgery, Oral Medicine, Oral Pathology, Oral Radiology and Endodontics, Mosby-Year Book, St. Louis, MO, US, vol. 104, No. 3, Aug. 18, 2007, pp. e26-e31, XP022198993.
Japanese Office Action (including English translation) issued in App. No. JP2021566308, dated Mar. 11, 2025, 4 pages.
Partial Supplementary European Search Report issued in App. No. EP20802623, dated Jan. 5, 2023, 21 pages.
Tran et al., "The influence of some vasoactive drugs on bone circulation", European Journal of Pharmacology, Elsevier Science, NL, vol. 52, No. 1, Nov. 1, 1978, pp. 109-114, XP023839065.

* cited by examiner

100

102  Providing a volume of at least one injectate comprising at least one therapeutic agent 104  Injecting the volume of the at least one injectate into a first bone site through a first lumen 106  Maintaining the volume of the at least one injectate within the first bone site in a localized state

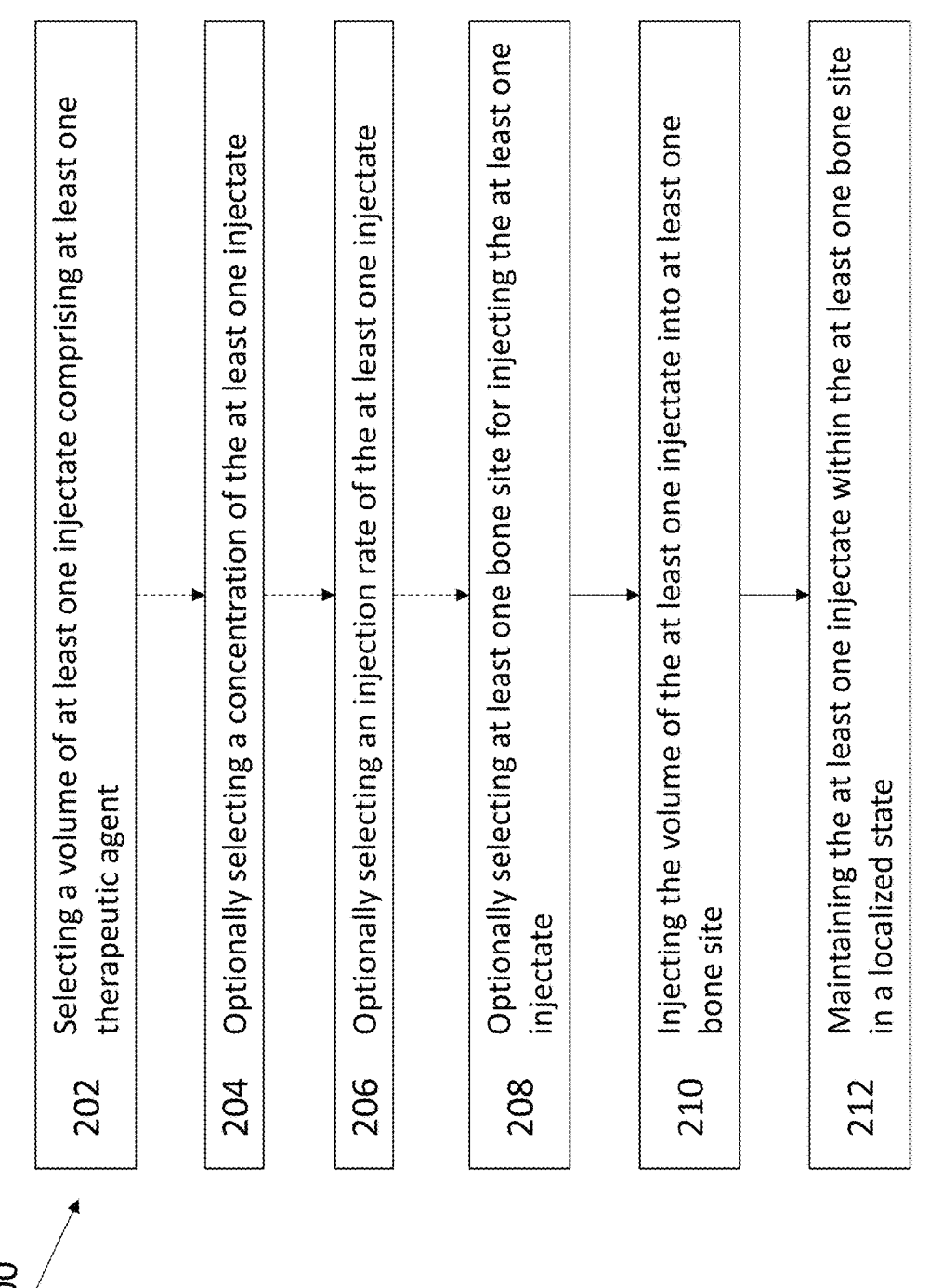

200

| 202 | Selecting a volume of at least one injectate comprising at least one therapeutic agent |

| 204 | Optionally selecting a concentration of the at least one injectate |

| 206 | Optionally selecting an injection rate of the at least one injectate |

| 208 | Optionally selecting at least one bone site for injecting the at least one injectate |

| 210 | Injecting the volume of the at least one injectate into at least one bone site |

| 212 | Maintaining the at least one injectate within the at least one bone site in a localized state |

FIG. 2

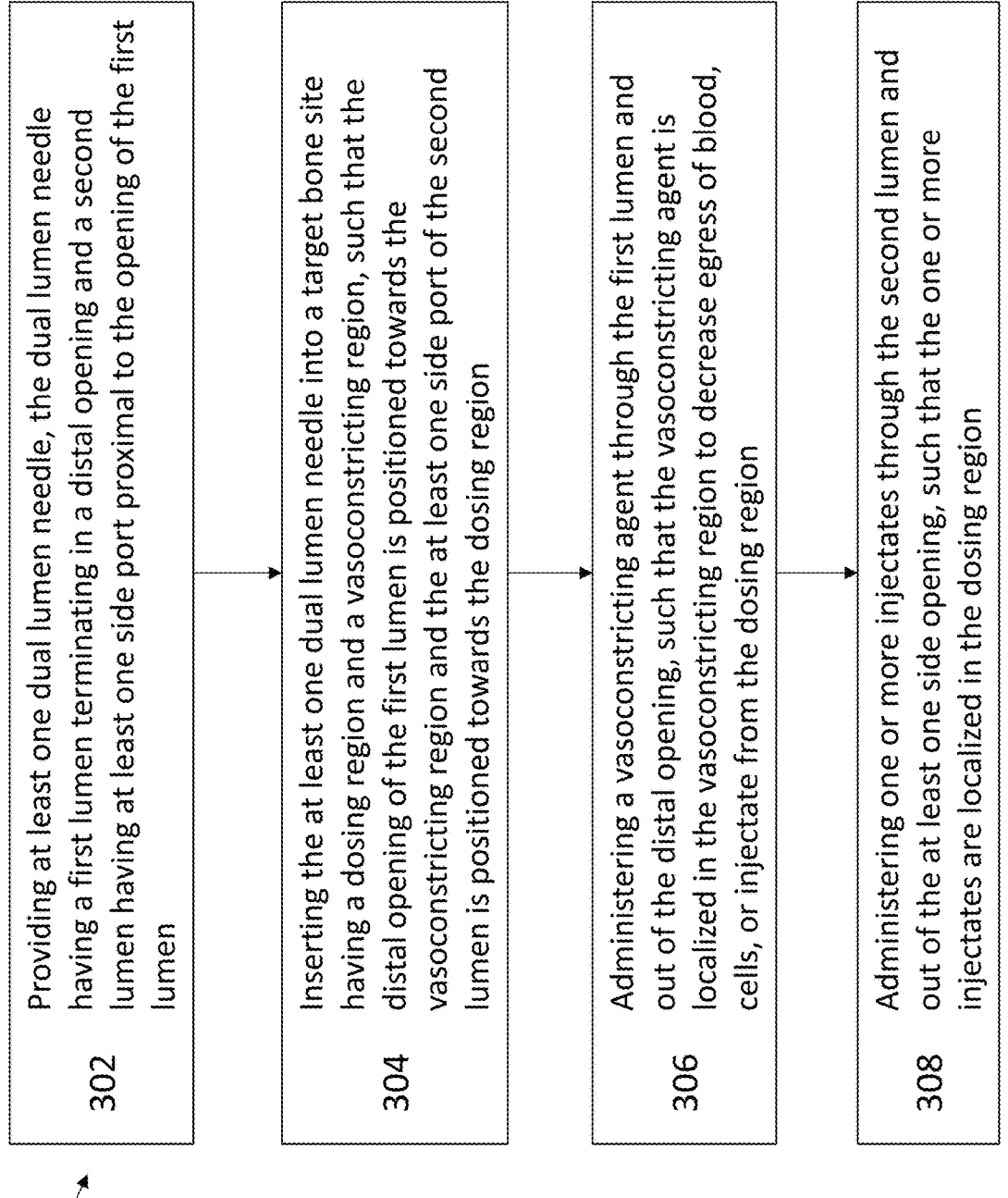

300

302 Providing at least one dual lumen needle, the dual lumen needle having a first lumen terminating in a distal opening and a second lumen having at least one side port proximal to the opening of the first lumen 304 Inserting the at least one dual lumen needle into a target bone site having a dosing region and a vasoconstricting region, such that the distal opening of the first lumen is positioned towards the vasoconstricting region and the at least one side port of the second lumen is positioned towards the dosing region 306 Administering a vasoconstricting agent through the first lumen and out of the distal opening, such that the vasoconstricting agent is localized in the vasoconstricting region to decrease egress of blood, cells, or injectate from the dosing region 308 Administering one or more injectates through the second lumen and out of the at least one side opening, such that the one or more injectates are localized in the dosing region

FIG. 3

MAXIMIZING DISTRIBUTION AND MINIMIZING WASHOUT OF INJECTATES IN BONE AND METHOD FOR ENHANCED ASPIRATE EXTRACTION

CROSS-REFERENCE TO RELATED APPLICATIONS

This application is the U.S. national phase application filed under 35 U.S.C. § 371 claiming benefit to International Patent Application No. PCT/US20/31919 filed May 7, 2020, which is entitled to priority under 35 U.S.C. § 119 (e) to U.S. Provisional Patent Application No. 62/844,592, filed May 7, 2019, the contents of which are each incorporated by reference herein in their entirety.

BACKGROUND OF THE INVENTION

Intraosseous (IO) drug and fluid administration have been used primarily in emergency settings when intravenous access is difficult or cannot be obtained. Due to the venules of bone being fragile with incomplete walls and to bone being a rigid compartment, drugs administered into bone under high pressures immediately leave the bone and enter systemic circulation in similar fashion to intravenous (IV) administration if they are flushed through with saline. Indeed, for most if not all purposes, IO administration is considered equivalent to IV administration. For example, the first study of IO administration was in dogs using iodinated contrast and imaged using fluoroscopy, and the contrast was observed to reach the heart in 4 seconds. Specific pharmacodynamic studies have been performed using certain drugs that corroborate this assumption. The IO route is typically used for resuscitation and vasoconstricting drugs are used in the advanced cardiovascular life support (ACLS) and pediatric advanced life support (PALS) resuscitation protocols.

However, immediate systemic distribution of drugs administered intraosseously is not wanted in every procedure. Targeted treatments to bone lose effectiveness if the treatments cannot be localized to the target bone site. Sample collection may be diluted or reduced if desired components are flushed out of the bone. In certain cases, treatments can be dangerous if the administered drug exits the bone and leads to systemic toxicity. Examples include but are not limited to stem cell harvest, intraosseous infection, tumor treatment, and osseous stabilization (such as vertebroplasty).

Thus, there is a need in the art for improved methods of maintaining injectates within a bone site. The present invention meets this need.

SUMMARY OF THE INVENTION

In one aspect, the present invention relates to a method of modulating the rate of egress and intraosseous distribution of an injectate, comprising the steps of: providing a volume of at least one injectate comprising at least one therapeutic agent; injecting the volume of the at least one injectate into a first bone site through a first lumen; and maintaining the volume of the at least one injectate within the first bone site in a localized state such that at least 15% to 95% of the volume is retained for at least 5 minutes to 2 hours.

In one embodiment, the at least one injectate further comprises at least one vasoactive agent. In one embodiment, the injecting step is preceded by a step of performing an administration of at least one first injectate at a pressure or rate such that connections between surrounding venules at the first bone site are opened by way of incomplete or fragile sinusoidal walls. In one embodiment, the pressure is selected from the group consisting of about: 10 psi, 20 psi, 30 psi, 40 psi, 50 psi, 60 psi, 70 psi, 80 psi, 90 psi, 100 psi, 200 psi, 300 psi, 400 psi, 500 psi, 600 psi, 700 psi, 800 psi, 900 psi, and 1000 psi. In one embodiment, the rate is selected from the group consisting of about: 0.1 μL/s, 1 μL/s, 10 μL/s, 50 μL/s, 0.1 mL/s, 0.2 mL/s, 0.3 mL/s, 0.4 mL/s, 0.5 mL/s, 0.6 mL/s, 0.7 mL/s, 0.8 mL/s, 0.9 mL/s, 1 mL/s, 2 mL/s, 3 mL/s, 4 mL/s, 5 mL/s, 6 mL/s, 7 mL/s, 8 mL/s, 9 mL/s, and 10 mL/s.

In one embodiment, a volume of at least one vasoactive agent is injected before the volume of the at least one injectate. In one embodiment, a volume of at least one vasoactive agent is injected after the volume of the at least one injectate. In one embodiment, a volume of the at least one vasoactive agent is injected simultaneously with the volume of the at least one injectate. In one embodiment, a volume of at least one vasoactive agent is injected in close proximity to a draining vein of bone. In one embodiment, the first bone site is positioned nonadjacent to a draining vein of bone.

In one embodiment, the at least one vasoactive agent is a vasoconstrictive agent selected from the group consisting of: a sympathomimetic, methoxamine hydrochloride, epinephrine, dobutamine, dopamine, norepinephrine, milrinone, midodrine hydrochloride, desglymidodrine, and an alpha-receptor agonist, stimulant or activator. In one embodiment, the at least one vasoactive agent is a vasodilative agent selected from the group consisting of: alpha or beta adrenergic receptor modulators, muscarine, histamine, dopamine receptor modulators, an organic nitrate, isosorbide mononitrate, a mononitrate, isosorbide dinitrate, a dinitrate, nitroglycerin, a trinitrate, minoxidil, sodium nitroprusside, hydralazine hydrochloride, nitric oxide, nicardipine hydrochloride, fenoldopam mesylate, diazoxide, enalaprilat, epoprostenol sodium, a prostaglandin, milrinone lactate, a bipyridine, and a dopamine D1-like receptor agonist, stimulant or activator. In one embodiment, the at least one therapeutic agent is selected from the group consisting of: an anti-tumor agent, an antiproliferative agent, an anti-angiogenic agent, a cytotoxic agent, an antimicrobial (including anti-bacterial and anti-fungal) agent, a cell-mobilizing agent, and a pain-relieving agent.

In one embodiment, the method further comprises a step of selecting an injection rate of the at least one injectate from the group consisting of about: 0.1 μL/s, 1 μL/s, 10 μL/s, 50 μL/s, 0.1 mL/s, 0.2 mL/s, 0.3 mL/s, 0.4 mL/s, 0.5 mL/s, 0.6 mL/s, 0.7 mL/s, 0.8 mL/s, 0.9 mL/s, 1 mL/s, 2 mL/s, 3 mL/s, 4 mL/s, 5 mL/s, 6 mL/s, 7 mL/s, 8 mL/s, 9 mL/s, and 10 mL/s. In one embodiment, the volume of the at least one injectate is selected from the group consisting of about: 0.1 μL, 1 μL, 10 μL, 50 μL, 100 μL, 500 μL, 1 mL, 2 mL, 3 mL, 4 mL, 5 mL, and 10 mL. In one embodiment, the volume of the at least one vasoactive agent is selected to reduce blood flow at the bone site by about 5%, 10%, 15%, 20%, 25%, 30%, 35%, 40%, 45%, 50%, 55%, 60%, 65%, 70%, 75%, 80%, 85%, 90%, or 95%. In one embodiment, the volume of the at least one therapeutic agent has a concentration selected from the group consisting of: greater than about 0 wt %, greater than about 5 wt %, greater than about 10 wt %, greater than about 15 wt %, greater than about 20 wt %, greater than about 25 wt %, greater than about 30 wt %, greater than about 35 wt %, greater than about 40 wt %, greater than about 45 wt %, greater than about 50 wt %, greater than about 55 wt %, greater than about 60 wt %, greater than about 65 wt %, greater than about 70 wt %, greater than about 75 wt %, greater than about 80 wt %, greater than about 85 wt %, greater than about 90 wt %, or greater than about 95 wt %.

In one embodiment, the method further comprises a step of extracting a volume of aspirate from one or more additional bone sites through one or more additional lumens after the step of maintaining the volume of the at least one injectate within the first bone site in a localized state, such that a pressure gradient is formed across a vasculature or a bone field between the first bone site having a first pressure and the one or more additional bone sites each having a pressure lower than the first pressure.

In one embodiment, the first lumen and the one or more additional lumens are positioned in a single device. In one embodiment, the first lumen is positioned in a first device and the one or more additional lumens are positioned in one or more additional devices. In one embodiment, the one or more additional bone sites are each between about 5 mm to about 500 mm distant from the first bone site. In one embodiment, the step of injecting and the step of extracting are performed at sequential depths at their respective bone sites.

In another aspect, the present invention relates to a method of enhancing aspirate yield from a bone site, comprising the steps of: providing a volume of at least one injectate; injecting the volume of the at least one injectate into a first bone site through a first lumen; and extracting a volume of aspirate from one or more additional bone sites through one or more additional lumens; wherein the first bone site and the second bone site are positioned between about 5 mm to 500 mm from each other; such that a pressure gradient is formed across a vasculature or a bone field between the first bone site having a first pressure and the one or more additional bone sites each having a pressure lower than the first pressure.

In one embodiment, the step of injecting and the step of extracting are performed at the same time. In one embodiment, the step of extracting is performed sequentially after the step of injecting. In one embodiment, the step of injecting and the step of extracting are performed at sequential depths at their respective bone sites. In one embodiment, the first lumen and the one or more additional lumens are positioned in a single device. In one embodiment, the first lumen is positioned in a first device and the one or more additional lumens are positioned in one or more additional devices.

In one embodiment, the method further comprises a step of selecting a positive injection pressure and a negative extraction pressure from the group consisting of about: 10 psi, 20 psi, 30 psi, 40 psi, 50 psi, 60 psi, 70 psi, 80 psi, 90 psi, 100 psi, 200 psi, 300 psi, 400 psi, 500 psi, 600 psi, 700 psi, 800 psi, 900 psi, and 1000 psi. In one embodiment, the method further comprises a step of selecting an injection rate and an extraction rate from the group consisting of about: 0.1 μL/s, 1 μL/s, 10 μL/s, 50 μL/s, 0.1 mL/s, 0.2 mL/s, 0.3 mL/s, 0.4 mL/s, 0.5 mL/s, 0.6 mL/s, 0.7 mL/s, 0.8 mL/s, 0.9 mL/s, 1 mL/s, 2 mL/s, 3 mL/s, 4 mL/s, 5 mL/s, 6 mL/s, 7 mL/s, 8 mL/s, 9 mL/s, and 10 mL/s.

In one embodiment, the volume of the at least one injectate and the volume of the aspirate are each selected from the group consisting of about: 0.1 μL, 1 μL, 10 μL, 50 μL, 100 μL, 500 μL, 1 mL, 2 mL, 3 mL, 4 mL, 5 mL, and 10 mL. In one embodiment, the volume of the aspirate is a percentage of the volume of the at least one injectate, the percentage selected from the group consisting of: 50%, 60%, 70%, 80%, 90%, and 100%. In one embodiment, the volume of the at least one injectate comprises a fluid. In one embodiment, the volume of the at least one injectate comprises at least one fluid agent selected from the group consisting of: a vasoactive agent, an anti-tumor agent, an antiproliferative agent, an anti-angiogenic agent, a cytotoxic agent, an antimicrobial (including anti-bacterial and anti-fungal) agent, a cell-mobilizing agent, and a pain-relieving agent.

In one embodiment, the vasoactive agent is a vasoconstrictive agent selected from the group consisting of: a sympathomimetic, methoxamine hydrochloride, epinephrine, dobutamine, dopamine, norepinephrine, milrinone, midodrine hydrochloride, desglymidodrine, and an alpha-receptor agonist, stimulant or activator. In one embodiment, the vasoactive agent is a vasodilative agent selected from the group consisting of: alpha or beta adrenergic receptor modulators, muscarine, histamine, dopamine receptor modulators, an organic nitrate, isosorbide mononitrate, a mononitrate, isosorbide dinitrate, a dinitrate, nitroglycerin, a trinitrate, minoxidil, sodium nitroprusside, hydralazine hydrochloride, nitric oxide, nicardipine hydrochloride, fenoldopam mesylate, diazoxide, enalaprilat, epoprostenol sodium, a prostaglandin, milrinone lactate, a bipyridine, and a dopamine D1-like receptor agonist, stimulant or activator. In one embodiment, the at least one fluid agent has a concentration selected from the group consisting of: greater than about 0 wt %, greater than about 5 wt %, greater than about 10 wt %, greater than about 15 wt %, greater than about 20 wt %, greater than about 25 wt %, greater than about 30 wt %, greater than about 35 wt %, greater than about 40 wt %, greater than about 45 wt %, greater than about 50 wt %, greater than about 55 wt %, greater than about 60 wt %, greater than about 65 wt %, greater than about 70 wt %, greater than about 75 wt %, greater than about 80 wt %, greater than about 85 wt %, greater than about 90 wt %, or greater than about 95 wt %.

In another aspect, the present invention relates to a method of localizing injectates within a bone site, comprising the steps of: providing at least one dual lumen needle, the dual lumen needle having a first lumen terminating in a distal opening and a second lumen having at least one side port proximal to the opening of the first lumen; inserting the at least one dual lumen needle into a target bone site having a dosing region and a vasoconstricting region, such that the distal opening of the first lumen is positioned towards the vasoconstricting region and the at least one side port of the second lumen is positioned towards the dosing region; administering a vasoconstricting agent through the first lumen and out of the distal opening, such that the vasoconstricting agent is localized in the vasoconstricting region to decrease egress of blood, cells, or injectate from the dosing region; and administering one or more injectates through the second lumen and out of the at least one side opening, such that the one or more injectates are localized in the dosing region.

In one embodiment, the method further comprises a step of extracting tissue using the at least one dual lumen needle by way of the at least one side port of the second lumen. In one embodiment, at least one additional needle is provided, the needle having at least one lumen. In one embodiment, the at least one additional needle is a single lumen needle. In one embodiment, the method further comprises a step of inserting the at least one additional needle into at least one bone site adjacent to the target bone site and aspirating using the at least one additional needle. In one embodiment, the at least one additional needle is a dual lumen needle having a first lumen terminating in a distal opening and a second lumen having at least one side port proximal to the opening of the first lumen. In one embodiment, the method further comprises a step of inserting the at least one additional dual lumen needle into at least one bone site adjacent to the target bone site and administering a vasoconstricting agent using the first lumen and distal opening of the at least one additional dual lumen needle. In one embodiment, the method further comprises a step of inserting the at least one additional dual lumen needle into at least one bone site adjacent to the target bone site and aspirating using a lumen of the at least one additional dual lumen needle.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

FIG. 2 is a flowchart depicting another exemplary method of maintaining injectates within a bone site.

FIG. 3 is a flowchart depicting an exemplary method of localizing injectates within a bone site.

DETAILED DESCRIPTION

Figure 1:
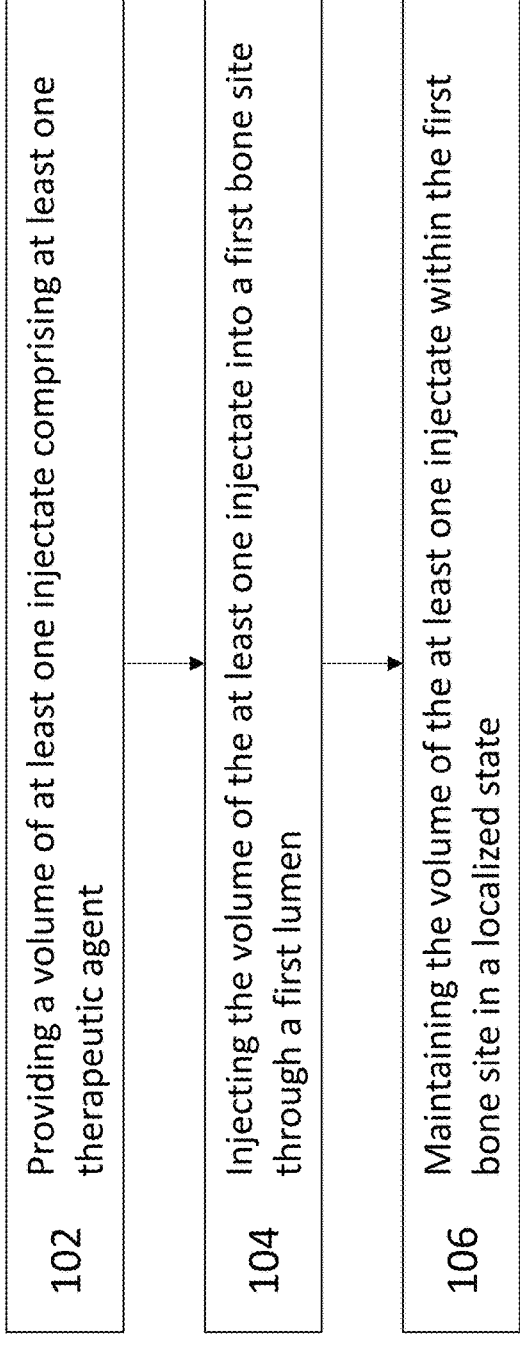
FIG. 1 is a flowchart depicting an exemplary method of maintaining injectates within a bone site.

The present invention provides methods of distributing agents into bone and the maintenance of those agents within bone. These methods include mechanical, rheological, pharmacological, and other methods. By maintaining injectates within a targeted location in bone and increasing their distribution in bone, the methods are useful for purposes including but not limited to increasing local concentration, improving therapeutic effectiveness, increasing duration of action, and decreasing systemic toxicity. These same methods can displace the contents of bone toward a harvesting instrument for purposes of collection with similar and complimentary methods. In some embodiments, the methods are useful for placing and distributing a structural augmentation substance such as cement or a biologic agent to augment bone. In some embodiments, the methods are useful for decreasing the egress of cells from a bone marrow cavity. In some embodiments, the methods are useful for displacing marrow contents toward a harvesting device. In some embodiments, the methods are useful for treating vascular or neural diseases within bone such as certain types of arthritis. In some embodiments, the methods are useful for treating disorders of bone that are related to abnormal intraosseous pressures. Without the risk of systemic distribution, the methods permit a larger dose than could be tolerated systemically to be administered intraosseously, maintained within the bone, and optionally aspirated or flushed out by one or more devices. The methods are useful for controlling the rate of egress of intraosseous distribution of agents or cells for a variety of purposes, including but not limited to: augmenting stem cell recovery in bone marrow aspiration, chemotherapy, medication delivery, treatment of infection, bone augmentation, and the like.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the compositions of the invention in prevention of the occurrence of tumor in the first place.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "inhibit," as used herein, means to suppress or block an activity or function by at least about ten percent relative to a control value. For example, the activity can be suppressed or blocked by 50% compared to a control value, by 75%, or by 95%.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a subject and includes: (a) preventing a disease related to an undesired immune response from occurring in a subject which may be predisposed to the disease; (b) inhibiting the disease, i.e. arresting its development: or (c) relieving the disease, i.e. causing regression of the disease.

The terms "effective amount" and "pharmaceutically effective amount" refer to a sufficient amount of an agent to provide the desired biological result. That result can be reduction and/or alleviation of a sign, symptom, or cause of a disease or disorder, or any other desired alteration of a biological system. An appropriate effective amount in any individual case may be determined by one of ordinary skill in the art using routine experimentation.

A "therapeutically effective amount" refers to that amount which provides a therapeutic effect for a given condition and administration regimen. In particular, "therapeutically effective amount" means an amount that is effective to prevent, alleviate or ameliorate symptoms of the disease or prolong the survival of the subject being treated, which may be a human or non-human animal. Determination of a therapeutically effective amount is within the skill of the person skilled in the art.

As used herein, the term "pharmaceutical composition" refers to a mixture of at least one compound of the invention with other chemical components and entities, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antimicrobial (e.g., anti-bacterial and anti-fungal) agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The phrase "biological sample" is used herein in its broadest sense. A sample may be of any biological tissue or fluid from which biomarkers of the present invention may be detected, extracted, isolated, characterized or measured. Examples of such samples include but are not limited to blood, lymph, urine, gynecological fluids, biopsies, amniotic fluid and smears. Samples that are liquid in nature are referred to herein as "bodily fluids." Biological samples may be obtained from a patient by a variety of techniques including, for example, by scraping or swabbing an area or by using a needle to aspirate bodily fluids. Methods for collecting various biological samples are well known in the art. Frequently, a sample will be a "clinical sample," i.e., a sample derived from a patient. Such samples include, but are not limited to, bodily fluids which may or may not contain cells, e.g., blood (e.g., whole blood, serum or plasma), urine, saliva, tissue or fine needle biopsy samples, and archival samples with known diagnosis, treatment and/or outcome history. Biological samples also include tissues, such as, frozen sections taken for histological purposes. The sample also encompasses any material derived by processing a biological sample. Derived materials include, but are not limited to, cells (or their progeny) isolated from the sample, proteins or nucleic acid molecules extracted from the sample. Processing of a biological sample may involve one or more of: filtration, distillation, extraction, concentration, inactivation of interfering components, addition of reagents, and the like.

The term "injectate" is used herein to refer to any injectable material. Injectable materials are typically traversable to a site of injection through a delivery lumen, and are commonly provided as a gas, a liquid, a solution, a gel, a mixture, a suspension, a cement, or a viscous paste.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Referring now to FIG. 1, an exemplary method 100 is depicted for modulating the rate of egress and intraosseous distribution of an injectate. Method 100 begins with step 102, wherein a volume of at least one injectate comprising at least one therapeutic agent is provided. In step 104, the volume of the at least one injectate is injected into a first bone site through a first lumen. In step 106, the at least one injectate is maintained within the first bone site in a localized state.

In some embodiments, the steps are performed in the order listed. In some embodiments, the steps are preceded by an optional first step of performing an administration of at least one first injectate at a pressure or rate such that connections between surrounding venules at the first bone site are opened by way of incomplete or fragile sinusoidal walls. The injectate can be any of the agents described elsewhere herein. Non-limiting examples of injectates include normal saline (about 0.9%) or a dilute heparinized solution. The pressure of administration can be about 10 psi, 20 psi, 30 psi, 40 psi, 50 psi, 60 psi, 70 psi, 80 psi, 90 psi, 100 psi, 200 psi, 300 psi, 400 psi, 500 psi, 600 psi, 700 psi, 800 psi, 900 psi, and 1000 psi. The rate of administration can be about 0.1 µL/s, 1 µL/s, 10 µL/s, 50 µL/s, 0.1 mL/s, 0.2 mL/s, 0.3 mL/s, 0.4 mL/s, 0.5 mL/s, 0.6 mL/s, 0.7 mL/s, 0.8 mL/s, 0.9 mL/s, 1 mL/s, 2 mL/s, 3 mL/s, 4 mL/s, 5 mL/s, 6 mL/s, 7 mL/s, 8 mL/s, 9 mL/s, and 10 mL/s.

In some embodiments, a volume of at least one vasoactive agent is also provided. The at least one vasoactive agent and the at least one injectate can be provided alone or in combination, with or without systemic delivery of therapeutic substances that may further augment the function of the intraosseously administered agents. In certain embodiments, the at least one vasoactive agent is injected before the volume of the at least one injectate. In certain embodiments, the at least one vasoactive agent is injected after the volume of the at least one injectate. In certain embodiments, the vasoactive agent is injected simultaneously with the volume of the at least one injectate. The site of injection for the at least one vasoactive agent and the at least one injectate can be the same site or different sites. Contemplated sites include close proximity to a draining vein of a bone or nonadjacent to a draining vein of bone. Vasoactive agent compositions, therapeutic agent compositions, injection rates, injection volumes, injection concentrations, and injection sites are described in detail elsewhere herein.

Therapeutic Agents

The present invention encompasses the use of any suitable therapeutic agents. Certain therapeutic agents may be more appropriate than others depending on the procedure and the desired effect. In various embodiments, the therapeutic agents are useful for treating a disease or disorder. In various embodiments, the therapeutic agents are useful for obtaining a tissue or cell sample.

In some embodiments, the therapeutic agent includes a solution or matrix that contains a biologic, such as a biologically active cell, which may be an autologous cell or an allogeneic cell, either of which may be cultured, augmented, differentiated, or genetically altered in any fashion. In some embodiments, the therapeutic agent contains a solution or matrix that can attract cells via cell signaling molecules.

In some embodiments, the therapeutic agents are useful for treating cancer. Cancer treating therapeutic agents include anti-tumor and chemotherapeutic agents such as cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diamminedichloroplatimun, mitoxantrone, CBDCA, levamisole, hexamethylmelamine, all-trans retinoic acid, gliadel and porfimer sodium).

Cancer treating therapeutic agents also include antiproliferative agents, which are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene). Additional examples of specific antiproliferative agents include, but are not limited to levamisole, gallium nitrate, granisetron, sargramostim strontium-89 chloride, filgrastim, pilocarpine, dexrazoxane, and ondansetron.

The cancer treating therapeutic agents can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclo-phosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

In certain embodiments, the therapeutic agents described herein comprise at least one antimicrobial agent. The antimicrobial agent can be an antifungal agent or an antibacterial agent. In one embodiment, the antibacterial agent is a broad-spectrum antibacterial agent. Suitable antibacterial agents include, but are not limited to, antistaphylococcal penicillin such as nafcillin or oxacillin or a first-generation cephalosporin such as cefazolin, third generation cephalosporins such as cefotaxime or ceftriaxone, linezolid Piperacillin-tazobactam, Ampicillin-sulbactam, Ticarcillin-clavulanate, doxycycline, minocycline, clindamycin, vancomycin, daptomycin, metronidazole, Amoxicillin-clavulanuate, the flouroquinolone family such as ciprofloxacin, levofloxacin, moxifloxacin, and Trimethoprim-sulfamethoxazol. Antifungal agents include, but are not limited to, lotrimazole, miconazole, ketoconazole, itraconazole and fluconazole, Amphotericin B, Anidulafungin, and Caspofungin.

In some embodiments, therapeutic agents are selected from, by way of non-limiting example, at least one nucleotide (e.g., a polynucleotide), at least one carbohydrate or at least one amino acid (e.g., a peptide). In specific embodiments, the therapeutic agent is a polynucleotide, an oligonucleotide, a gene expression modulator, a knockdown agent, an siRNA, an RNAi agent, a dicer substrate, an miRNA, an shRNA, an antisense oligonucleotide, or an aptamer. In other embodiments, the therapeutic agent is an aiRNA (Asymmetric RNA duplexes mediate RNA interference in mammalian cells. Xiangao Sun, Harry A Rogoff, Chiang J Li Nature Biotechnology 26, 1379-1382 (2008)). In certain embodiments, the therapeutic agent is a protein, peptide, dominant-negative protein, enzyme, antibody, or antibody fragment. In some embodiments, the therapeutic agent is a carbohydrate, or a small molecule. In some embodiments, the therapeutic agent is an abiotic, synthetic polymer. In some embodiments, the therapeutic agents can include autologous or allogenic stem cell grafts which may or may not be cultured or genetically altered.

In some embodiments, the therapeutic agents include cell mobilizing agents. The cell mobilizing agents can work through one or more mechanisms, including but not limited to: mobilizing cells from their native milieu; blocking the inhibition of cell departure; decreasing adhesion of cells to their surrounding environment; and modulating the neural or cellular control that dictate the stability, ingress, or egress of cells from their milieu. In some embodiments, the cell mobilizing agents can include any suitable composition that can augment cell yield by modulating the nervous system regulation of cell mobilization, by decreasing adherence to the native tissue or creating a cell mobilizing effect, either directly or indirectly. Cells may be mobilized into the surrounding extracellular milieu/matrix which may include the surrounding vascular space; in the case of bone marrow, this may be into the surrounding capillary bed and sinusoids.

Non-limiting categories of agents that may be used include currently known and yet to be discovered classes of proteins and receptors known to control the movement of cells out of tissue or retention of cells in tissue. These may include combinations, for example inhibition of $\alpha_9\beta_1$ by BOP (antibody or other small molecule selective inhibiter) and AMD3100 in combination. These include broad categories such as: modulation of the integrin family such as the VLA-4 molecule inhibitors firategast, UNII-OJY3 SK9H5F, BI05192, and derivatives thereof; modulation of the CXCL12/CXCR4 interaction such as the CXCR4 inhibitor plerixafor; modulation of the CXCR7 molecule; CXCL12 analogues; modulation of the nerve/stem cell interaction such as the dopamine receptors (1-5 subtypes) and noradrenergic alpha and beta receptors and all such receptors for the catecholamines, their precursors and derivatives; modulators of their receptors or modulators of the uptake of the neurotransmitters from the synapse/site of action; catecholamine degradation inhibitors such as inhibitors of catechol-O-methyltransferases (COMT) or amination by monoamine oxidases (MAO) enzymes; modulators of downstream cascade of catecholamine receptors such as adenylate cyclase and alternative phosphoinositide 3-kinase (PI3K)/Akt pathways; agonists and blockers of catecholamine receptors a1, a2, b1, b2, and b3; catecholamine precursors such as L-Phenylalanine, L-Tyrosine, and L-DOPA; dopamine agonists such as aripiprazole, phencyclidine, quinpirole, salvinorin A, apomorphine, bromocriptine (Parlodel), cabergoline (Dostinex), ciladopa, dihydrexidine, dinapsoline, doxanthrine, epicriptine, lisuride, pergolide, piribedil (Pronoran and Trivastal), pramipexole (Mirapex and Sifrol), propylnorapomorphine, quinagolide (Norprolac), ropinirole, rotigotine, roxindole, sumanirole, fenoldopam selective for dopamine receptor D1, cocaine, amphetamines; dopamine reuptake inhibitors such as buproprion altropane (O-587), Amfonelic acid (WIN 25978), Amineptine (has a reasonable degree of selectivity for dopamine over norepinephrine reuptake inhibition), BTCP (GK-13), 3C-PEP (extremely potent and selective for dopamine transporter), DBL-583, Difluoropine (O-620), GBR-12783, GBR-12935, GBR-13069, GBR-13098, GYKI-52895, Iometopane (β-CIT, RTI-55), Methylphenidate, Ethyphenidate, Modafinil, Armodafinil, RTI-229, Vanoxerine (GBR-12909), Haloperidol, Chlorpromazine, Eticlopride, Pimozide, Chlorpromazine, Eticlopride; desipramine and other drugs that inhibit the reuptake of norepinephrine; DRD1, DRD2, DRD3, DRD4, DRD4 receptor agonists, and antagonists such as eticlopride; nicotine; b2-adrenergic agonists such as clenbuterol; alpha9 integrin agonists; BOP, N-(Benzene-sulfonyl)-L-prolyl-L-O-(1-pyrrolidinylcarbonyl)tyrosine); VLA-4 antagonists such as trans-4-[1-[[2-(5-Fluoro-2-methylphenylamino)-7-fluoro-6-benzoxazolyl] acetyl]-(5S)-[methoxy(methyl)amino]methyl-(2S)-pyrrolidinylmethoxy]cyclohexanecarboxylic acid, natalizumab, and BI05192; matrix metalloproteinases and their inducers such as Me6TREN; prolyl hydroxylase inhibitors such as dimethyloxallyl glycine (DMOG); the chemokine GRObeta; sulfated colominic acid; beta-chemokine CCL15; panax notoginseng saponins; VEGF; ALT-1188; P2RY14 agonists such as MRS2690; UDP-glucose; gamma-tocotrienol; TGF β, TGF-β1, and Substance P; modulation of the adhesion molecules such as VCAM-1; interaction with the integrins such as VLA-4 (α9β1); G-protein coupled receptors such as P2Y purinocepter-14; S1P-1 modulators including ACT-128800, SEW2871, GSK2018682, FTY720, MRS 2690, and dopamine; various endocrine targets such as NOTCH protein (parathyroid hormone); granulocyte colony-stimulating factor (G-CSF) and analogs (filgrastim); PEGylated and glycosylated versions of G-CSF; granulocyte macrophage colony-stimulating factor (GM-CSF); macrophage colony stimulating factor (M-CSF); tyrosine kinase 3 (FLT-3); ancestim; stem cell factor; AMD3100; TG-0054; KRP203; 4F-benzoyl-TN14003; POL6326; P2G, a mutant protein of SDF-1β; CTCE-0021; CS549, a pepducin such as ATI-2341; a cytokine (such as interleukin-1, interleukin-3, interleukin-6, interleukin-7, interleukin-11, interleukin-12); a metalloproteinase; a serine protease; a cysteine protease; a peptidase; a chemokine; and the like. Non-selective agents such as heparin, sulfate and derivatives, and amide group anesthetics such as lidocaine are also contemplated.

In some embodiments, the therapeutic agent can include any suitable composition that can reduce the sensation of pain. Non-limiting examples include one or more of lidocaine, prilocaine, tetracaine, benzocaine, procaine, mepivacaine, bupivacaine, etidocaine, tropacocaine, piperocaine, stovaine, cyclomethylcaine, parethoxycaine, diclonine, falicain, pramoxine, amolanone, phenacaine, diperodon, dibucaine, and the like.

Vasoactive Agents

Studies have been performed on the effect of vasoactive drugs on blood flow through bone marrow and on the vascular resistance of circulation in bone marrow, showing that these drugs affect the rate at which they arrive in systemic circulation. Vasoactive drugs have been used to restrict blood flow to the skin and to subcutaneous tissues, such as the combination of an anesthetic (e.g., lidocaine) with epinephrine. The epinephrine decreases blood flow to the skin, thereby decreasing the rate at which lidocaine is absorbed into circulation and allowing greater doses to be given without systemic toxicity.

In some embodiments, the present invention provides methods of using vasoactive drugs to modulate blood flow. A vasoactive substance may be pharmacologically synergistic or additive to an intended purpose, for example alpha and beta adrenergic receptor or a selective or non-selective dopamine receptor modulation to mobilize stem cells. In one embodiment, an injectate that causes the egress of stem cells from their niche can be combined with a vasoconstricting substance to decrease blood flow, preventing the mobilized cells from being lost to systemic circulation. The administration of vasoactive drugs thereby maintains cells which have exited their niche into the sinusoids and/or venules within bone. In some embodiments, a vasodilative substance can be used to flush out unwanted injectates localized within a bone site. The administration of vasoactive drugs thereby enables the controlled termination of a procedure wherein further maintenance of an injectate at a bone site is no longer desired.

In some embodiments, the vasoactive agent includes vasoconstrictive agents. Vasoconstrictive agents include, but are not limited to: a sympathomimetic, specific and nonspecific modulators of alpha and beta adrenergic receptors and subtypes as well as modulators of dopamine receptors including specific modulation of dopamine subtypes, direct and indirect agonists such as dopamine reuptake inhibitors and dopamine releasing agents, methoxamine hydrochloride, epinephrine, norepinephrine, dobutamine, dopamine, milrinone, midodrine hydrochloride, desglymidodrine, and the like.

In some embodiments, the vasoactive agent includes vasodilative agents. Vasodilative agents include, but are not limited to: alpha or beta adrenergic receptor modulators, muscarine, histamine, dopamine receptor modulators, an organic nitrate, isosorbide mononitrate, a mononitrate, isosorbide dinitrate, a dinitrate, nitroglycerin, a trinitrate, minoxidil, sodium nitroprusside, hydralazine hydrochloride, nitric oxide, nicardipine hydrochloride, fenoldopam mesylate, diazoxide, enalaprilat, epoprostenol sodium, a prostaglandin, vasoactive intestinal peptide (VIP), substance P, Niacin, carbon dioxide, natriuretic peptides, heparin, bradykinin, L-arginine, histamine and histamine agonists, antihistamines, milrinone lactate, a bipyridine, a dopamine D1-like receptor agonist, stimulant or activator, and the like.

In some embodiments, vasoconstrictive and vasodilative agents can be used to modulate the intraosseous pressure for purposes of modulating the dose of bone. In some embodiments, vasoconstrictive and vasodilative agents can be used to modulate the intraosseous pressure as a primary endpoint to treat disease.

Additives

In various embodiments, the injectate compositions of the present invention may further comprise additional additives including medicinal agents, pharmaceutical agents, carriers, buffers, adjuvants, dispersing agents, diluents, and the like depending on the intended use and application. In various embodiments, the additives can be used to modify certain attributes of the composition, including but not limited to viscosity, lipid solubility, hydrophobicity, hydrophilicity, pH, polarity, and the like.

Examples of suitable pharmaceutical carriers, excipients and/or diluents are well known in the art and include, but are not limited to, a gum, a starch (e g. corn starch, pregelatinized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Pharmaceutically acceptable carriers for liquid formulations are aqueous or non-aqueous solutions, suspensions, emulsions or oils, Examples of non-aqueous solvents are propylene glycol, polyethylene glycol, and injectable organic esters such as ethyl oleate. Examples of oils are those of animal, vegetable, or synthetic origin, for example, peanut oil, soybean oil, olive oil, sunflower oil, turmeric oil, fish-liver oil, another marine oil, or a lipid from milk or eggs.

Aqueous carriers include water, alcoholic/aqueous solutions, emulsions or suspensions, including saline and buffered media such as phosphate buffered saline solutions, water, emulsions, such as oil/water emulsions, various types of wetting agents, sterile solutions etc. Compositions comprising such carriers can be formulated by well-known conventional methods. Suitable carriers may comprise any material which, when combined with the biologically active compound of the invention, retains the biological activity. Preparations for parenteral administration may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles may include sodium chloride solution, Ringer's dextrose, dextrose and sodium chloride, lactated Ringer's, or fixed oils. Intravenous vehicles may include fluid and nutrient replenishes, electrolyte replenishers (such as those based on Ringer's dextrose), and the like. Preservatives and other additives may also be present including, for example, antimicrobials, anti-oxidants, chelating agents, and inert gases and the like, in addition, the pharmaceutical composition of the present invention might comprise proteinaceous carriers, e.g., serum albumin or immunoglobulin, such as of human origin.

The compositions provided herein may also be administered as controlled-release compositions, i.e. compositions in which the active ingredient is released over a period of time after administration. Controlled- or sustained-release compositions include formulation in lipophilic depots (e.g. fatty acids, waxes, oils). In another embodiment, the composition is an immediate-release composition, i.e. a composition in which all the active ingredient is released immediately after administration.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials.

Methods of Administration

As described elsewhere herein, the methods of the present invention modulate modes of administration to control the rate of egress and intraosseous distribution of an injectate. In some embodiments, the methods modulate the mode of injectate administration for maximum retention within a bone site.

Referring now to FIG. 2, an exemplary method 200 is depicted for modulating the rate of egress and intraosseous distribution of an injectate. Method 200 begins with step 202, wherein a volume of at least injectate comprising at least one therapeutic agent is selected. In step 204, a concentration of the at least one therapeutic agent is optionally selected. In step 206, an injection rate of the at least one injectate is optionally selected. In step 208, at least one bone site for injecting the at least one injectate is optionally selected. In step 210, the volume of the at least one injectate is injected into at least one bone site. In step 212, the at least one injectate is maintained within the at least one bone site in a localized state.

In certain embodiments, the methods can be described as retaining a percentage of a volume of injectate at an injection site or within a target bone. For example, the methods can retain at least 10%, 15%, 20%, 25%, 30%, 35%, 40%, 45%, 50%, 55%, 60%, 65%, 70%, 75%, 80%, 85%, 90%, or 95% of the volume of an injectate. In some embodiments, the retention percentage can be described as a factor of time. For example, the methods can retain at least 15% of the volume of an injectate for at least about 0.5 minutes, 1 minute, 2 minutes, 5 minutes, 10 minutes, 30 minutes, 60 minutes, 120 minutes, 24 hours, or 48 hours after injection.

In certain embodiments, the methods of the present invention optionally include steps for selecting the volumes and concentrations of injectate, including therapeutic agents, vasoactive agents, and combinations thereof. The volumes and concentrations can be selected for certain factors such as effective amounts of vasoactive agents, effective amounts of therapeutic agents, and the type of bone and size of bone associated with a bone site. In some embodiments, the volume and concentration of vasoactive agents can be selected to reduce blood flow at a bone site by about 5%, 10%, 15%, 20%, 25%, 30%, 35%, 40%, 45%, 50%, 55%, 60%, 65%, 70%, 75%, 80%, 85%, 90%, or 95%. A therapeutically effect volume and concentration of therapeutic agent may be dependent upon the type of therapeutic agent, the condition to be treated or prevented, and the like. In some embodiments, the therapeutic agent is present at greater than about 0 wt %, greater than about 5 wt %, greater than about 10 wt %, greater than about 15 wt %, greater than about 20 wt %, greater than about 25 wt %, greater than about 30 wt %, greater than about 35 wt %, greater than about 40 wt %, greater than about 45 wt %, greater than about 50 wt %, greater than about 55 wt %, greater than about 60 wt %, greater than about 65 wt %, greater than about 70 wt %, greater than about 75 wt %, greater than about 80 wt %, greater than about 85 wt %, greater than about 90 wt %, or greater than about 95 wt %. Typical volumes injectable into bone can range between about 0.1 µL, 1 µL, 10 µL, 50 µL, 100 µL, 500 µL, 1 mL, 2 mL, 3 mL, 4 mL, 5 mL, 10 mL, 20 mL, 50 mL, and the like. In situations where the bone is washed multiple times with sequential therapeutics, the volume can be described as a cumulative volume, such as a cumulative volume between about 100 mL and 1000 mL. It should be understood that a treatment or procedure may call for greater volumes of injectate, in which case the total volume can be injected over a series of smaller volumes.

In certain embodiments, the methods of the present invention optionally include steps for selecting the injection rates of injectate. The injection rate can be about 0.1 µL/s, 1 µL/s, 10 µL/s, 50 µL/s, 0.1 mL/s, 0.2 mL/s, 0.3 mL/s, 0.4 mL/s, 0.5 mL/s, 0.6 mL/s, 0.7 mL/s, 0.8 mL/s, 0.9 mL/s, 1 mL/s, 2 mL/s, 3 mL/s, 4 mL/s, 5 mL/s, 6 mL/s, 7 mL/s, 8 mL/s, 9 mL/s, 10 mL/s, and the like. In some embodiments, a vasoactive agent and a therapeutic agent are injected at different rates. In some embodiments, the injection rate is constant. In some embodiments, the injection rate is variable, such that the injection rate increases over time or decreases over time. For example, the injection rate can be varied over a range of between about 0.1 µL/s to 0.5 µL/s, 0.5 µL/s to 1 µL/s, 1 µL/s to 5 µL/s, 1 µL/s to 0.1 mL/s, 0.1 mL/s to 0.5 mL/s, 0.5 mL/s to 1 mL/s, 1 mL/s to 5 mL/s, 1 mL/s to 10 mL/s, and the like. It should be understood that the injection rate is varied depending on the viscosity of the injectate, the volume of the injectate, the density of the bone site, and the like. In certain embodiments, the viscosity of the injectate can be varied for both a therapeutic effect as well as a dose area effect. Viscosity can range from about 5 to 800 cP (800 cP being about twice the reported viscosity of bone marrow of some mammals).

In certain embodiments, the methods of the present invention optionally include steps for selecting the anatomical location of injectate. For example, injectate injected near draining veins of a bone are more likely to egress into systemic circulation at a faster rate than injectate injected farther from draining veins. Vasoactive agents injected near vasculature of a bone are more likely to modulate circulation in and out of bone than vasoactive agents injected farther from vasculature of a bone. In some embodiments, injectate can be injected at bone sites that are distant from draining veins. In some embodiments, vasoactive agents can be injected in closer proximity to draining veins than therapeutic agents so as to limit the vasoactive effect to the outflow/inflow of blood. In some embodiments, vasoactive agents can be injected into tissue surrounding a bone site targeted for therapeutic agent injection. In some embodiments, vasoactive agents can be administered systemically prior to the injection of therapeutic agent into a bone site. In some embodiments, the vasoactive agents can be placed in an artery-feeding bone.

In certain embodiments, the steps of the methods are augmented using pressure-based means. For example, as a volume of injectate is injected into a first bone site, one or more volumes of aspirates are extracted from one or more additional bone sites. A pressure gradient is thereby formed across a vasculature or a bone field between the first bone site of injection and the one or more additional bone sites of extraction, wherein the first bone site has a higher pressure, the one or more additional bone sites each have a pressure lower than the pressure of the first bone site, causing aspirate to migrate towards the one or more additional bone sites. The one or more volumes of aspirate can comprise any suitable or desired material, such as injectate, bone, blood, cells, marrow, and the like. Timing of injectate injection and material removal can be simultaneous or staggered. In some embodiments, the injection and removal can be performed using a single device with two lumens, a first lumen for injectate injection and a second lumen for material removal. Material removal can thereby be performed at the same site of injection. In some embodiments, the injection and removal can be performed using two or more separate devices, thereby injecting injectate at a first site and removing material from one or more additional sites. The one or more additional sites can each be immediately adjacent or separated from the first site by a small distance, such as between about 5 mm to about 50 mm. In some embodiments, the one or more additional sites are remote from the first site by about 50 mm to about 500 mm. In an exemplary embodiment, the simultaneous administration of injectate in one part of a bone and aspiration of material in another part of bone extends the field of injectate beyond what is achievable with a single needle by creating a pressure differential lower than the venous system making preferential flow to an aspiration needle compared to venous exit, and by creating a complimentary negative pressure drawing injectate across a bone field toward an aspiration needle rather than being forced into the venous system by a single pressure head. In some embodiments, the viscosity of the injectate can be selected for optimal displacement of in-situ marrow within bone sinusoids, similar to the manner in which injectate used for extracting oil from oil sands is matched for optimal displacement of oil. The contents of bone, including marrow, cells, infectious particles, and tumors, are displaced toward a needle or other device creating a negative pressure for harvest.

In certain embodiments, the steps of the methods are augmented using mechanical means. For example, the methods can employ a first device that distributes injectate in multiple locations either simultaneously or in series, such as in multiple sequential depths. The first device can be used in combination with a second device aspirating with a matching negative pressure at multiple different locations complementary to the multiple locations of the first device. In some embodiments, the first device, the second device, or both can comprise several apertures through which injectate or aspirate can pass through. The several apertures can be individually isolated to selectively distribute injectate at various injection sites and depths and to selectively withdraw aspirate at various aspiration sites and depths as desired, thereby maintaining physiological pressure and "pulling" fluids across an aspiration field. The process may be repeated at various locations and at various depths until the entire aspiration field between the first and second devices has been dosed or harvested.

Figure 5:
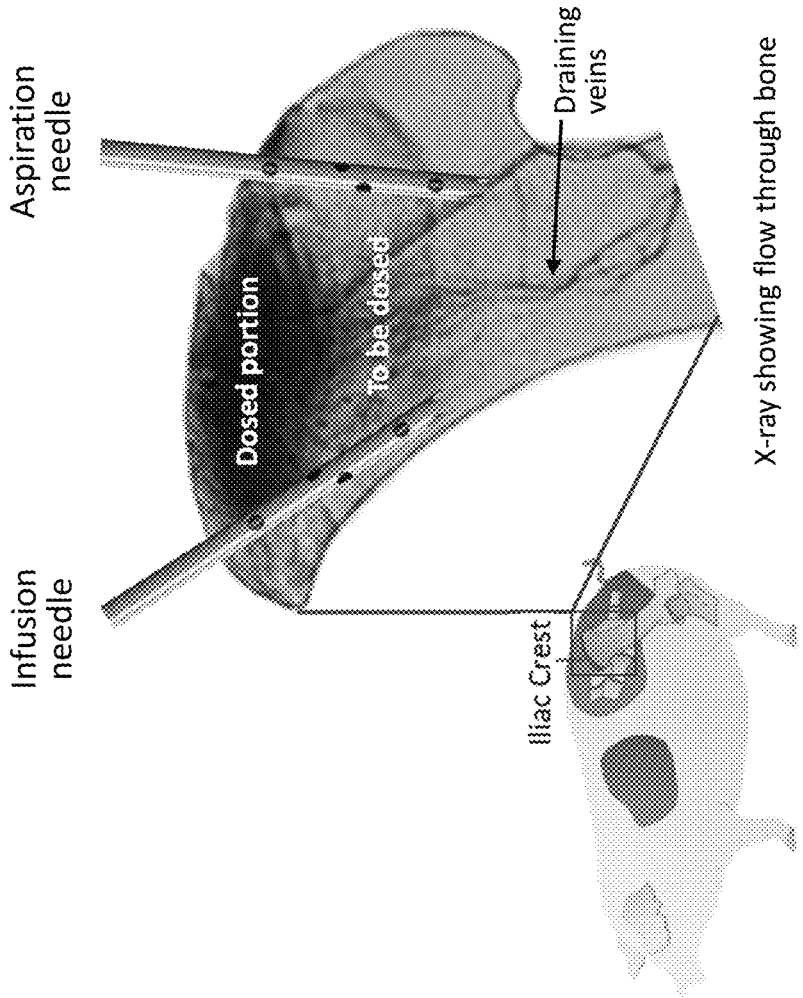
FIG. 5 depicts a diagram of preparing a target bone site for maintaining injectates within a bone site using dual lumen needles.
Figure 6:
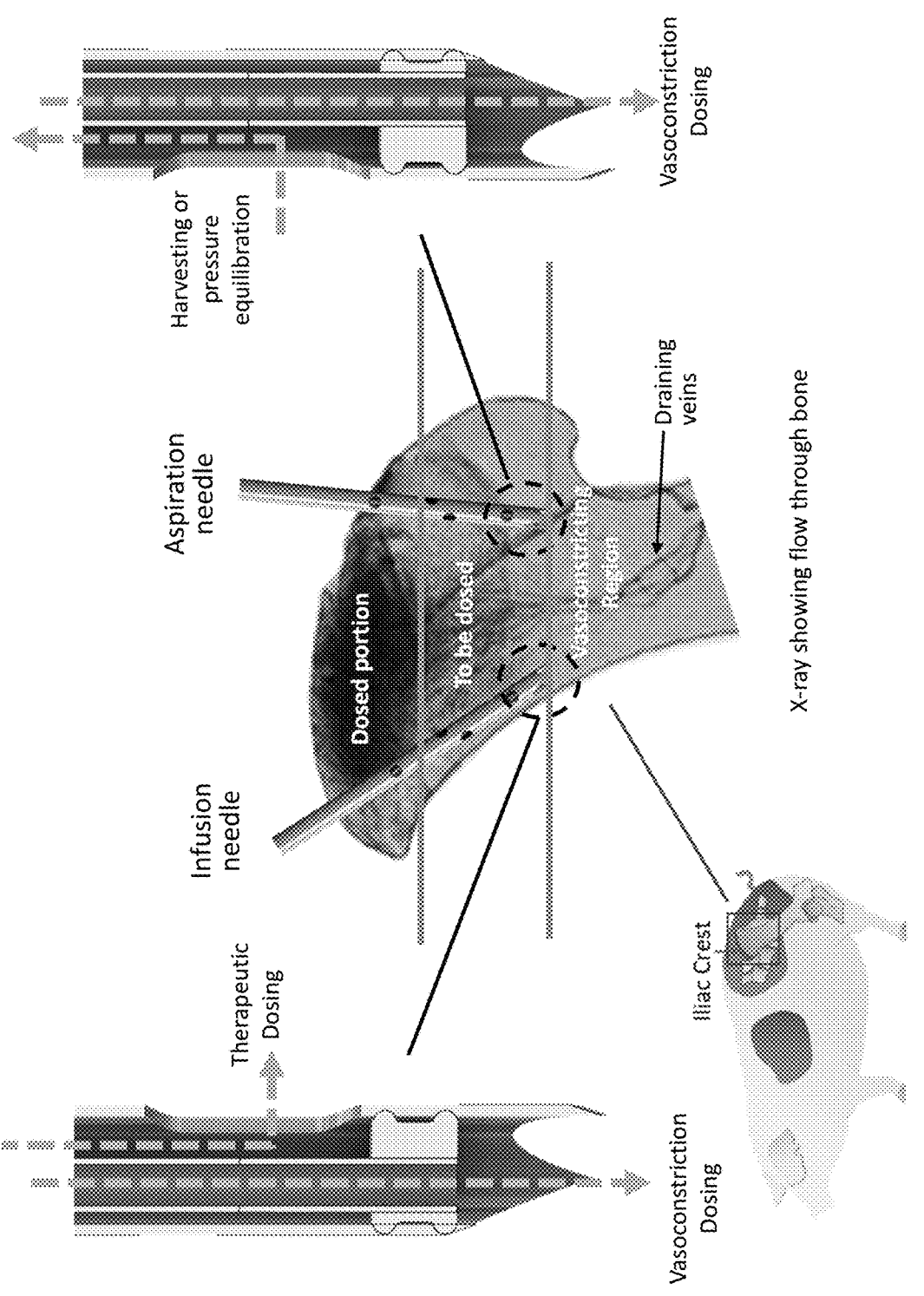
FIG. 6 depicts a diagram demonstrating an exemplary method of maintaining injectates within a bone site.

In one embodiment, methods and drugs can be combined to optimize their effects. A target site of bone can be flanked by at least one dual lumen needle, wherein one lumen exits the needle distally and the other lumen is situated to access one or more numerous side holes. For example, referring now to FIG. 3 (and illustrated in FIG. 4 through FIG. 6), an exemplary method 300 is depicted. Method 300 separates drugs administered through each lumen of a needle and is advantageous for localizing each drug. For example, if vasoconstriction were not wanted throughout an entire bone but only into a draining vein, a distal lumen opening can be used to administer a vasoconstricting agent to decrease the egress of blood, cells, or a therapeutic agent or drug from bone while leaving a treatment area without vasoconstriction in the case it may impair flow of therapeutic within the treatment area of the bone.

Figure 4:
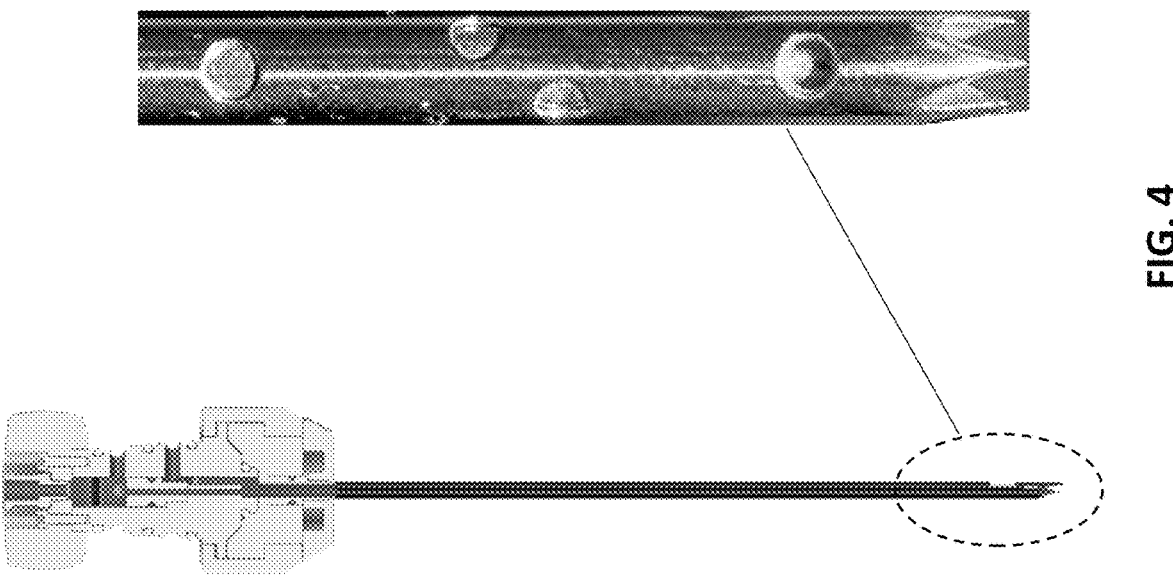
FIG. 4 depicts (left) a diagram of an exemplary dual lumen needle and (right) a magnified view of a dual lumen needle tip showing a distal opening to a first lumen and several closeable apertures to a second lumen at varying positions.

Method 300 begins with step 302, wherein at least one dual lumen needle is provided, the dual lumen needle having a first lumen terminating in a distal opening and a second lumen having at least one side port proximal to the opening of the first lumen (shown in FIG. 4). In step 304, the at least one dual lumen needle is inserted into a target bone site having a dosing region and a vasoconstricting region, such that the distal opening of the first lumen is positioned towards the vasoconstricting region and the at least one side port of the second lumen is positioned towards the dosing region (shown in FIG. 5, wherein the target bone site is an iliac crest). In step 306, a vasoconstricting agent is administered through the first lumen and out of the distal opening, such that the vasoconstricting agent is localized in the vasoconstricting region to decrease egress of blood, cells, or injectate from the dosing region. In step 308, one or more injectates are administered through the second lumen and out of the at least one side opening, such that the one or more injectates are localized in the dosing region (shown in FIG. 6).

In some embodiments, the same dual lumen needle is used to aspirate, extract, and harvest tissue (such as blood and cells), such as through the at least one side port of the second lumen. In some embodiments, one or more additional needles can be provided, each needle having at least one lumen. For example, the additional needle can be a single lumen needle or a dual lumen needle having a first and second lumen as described above. In some embodiments, the one or more additional dual lumen needles each administer a vasoconstricting agent through a distal opening of a first lumen, such that the coverage of the vasoconstriction agents is increased. The one or more additional needles may be used for any desired purpose, including but not limited to the administration of further injectates, the extraction and harvesting of tissue (such as blood and cells) across an area via a pressure gradient, the passive or active relief of liquid pressure within the target bone site for pain relief, and combinations thereof, through a single lumen or the respective second lumens of each dual lumen needle. Exemplary applications of the described methods include administration of an agent that causes egress of cells out of the niche into the sinusoids and using a separate drug through a separate lumen to maintain those cells in the bone by vasoconstriction.

In certain embodiments, the steps of the methods are augmented using physical or electrical means. For example, physical means of enhancing egress and intraosseous distribution of an injectate can be achieved by applying a vibration to a bone site, such as by sonication or massage. Physical means can also include external restriction of blood flow, such as by a temporary cuff or tourniquet or a cold compress applied to tissue in the vicinity of a bone site. As described elsewhere herein, physical means can also include a step of performing a forceful flush of an injectate to prepare an injection site. In some embodiments, the injectate can include charged or magnetic particles, such that the distribution of the injectate can be controlled through the application of an electrical or a magnetic field. In some embodiments, the injectate modulates the pH of the marrow space. In some embodiments, the injectate contains an anticoagulant.

In some embodiments, the various means of augmenting the steps of the methods, including but not limited to pharmacological means, pressure-based means, mechanical means, physical means, and electrical means, area used in combination.

The various method steps of modulating mode of injectate administration are equally applicable to fluid aspiration, should a treatment or procedure call for it. Fluid aspiration can be performed prior to, concurrently, or after a time period of injectate administration. Each pharmacologically active therapeutic agent has a time curve for peak effect. In some embodiments, fluid aspiration can be performed after peak effect has been achieved. For example, for the purpose of augmenting stem cell recovery during bone marrow aspiration, stem cells can be harvested at time points of 0, 5, 10, 15, 20, 25, 30, 35, 40, 45, 50, 55, 60, 65, 70, 75, 80, 85, 90, or more than 90 minutes.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Maximizing Distribution and Minimizing Washout of Fluid Injected in Bone The results described herein demonstrate that vasoactive agents enhance localized retention of fluid agents injected in bone. Injection rates and injection sites also enhance localized retention of fluid agents injected in bone. Anatomic placement affects the distribution and duration of injectate in bone. It also demonstrates that at the given viscosity of the iodinated contrast injected, it does not fill the entire bone and therefore a second needle can be placed to either administer fluid or provide a negative pressure for increased distribution.

Figure 7:
FIG. 7 is a fluoroscopic image of a contrast dye administrated into a subject's bone at a rate of 0.5 mL/second maximum distribution. The administration rate combined with the given viscosity does not adequately displace current blood volume in the sinusoids of the bone.

FIG. 7 is a fluoroscopic image of a contrast dye administrated into a subject's bone at a rate of 0.5 mL/second maximum distribution. The administration rate combined with the given viscosity does not adequately displace current blood volume in the sinusoids of the bone.

Figure 8:
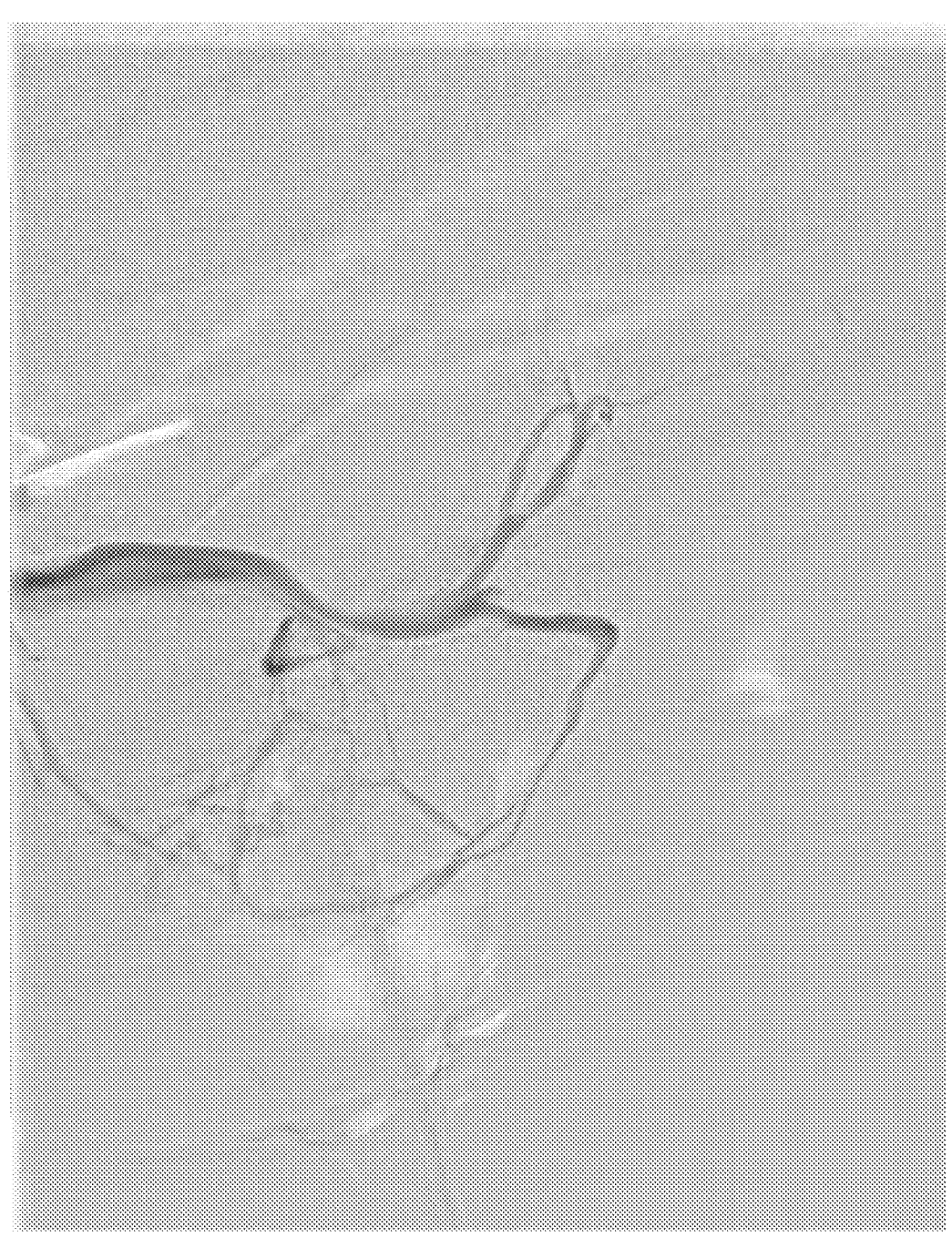
FIG. 8 is a fluoroscopic image of a contrast dye administrated into a subject's bone at a rate of 10 mL/second maximum distribution. The administration rate is too high, leading the contrast dye to immediately enter circulation with no retention in the bone.

FIG. 8 is a fluoroscopic image of a contrast dye administrated into a subject's bone at a rate of 10 mL/second maximum distribution. The administration rate is too high, leading the contrast dye to immediately enter circulation with no retention in the bone. This may be improved or obviated with additional negative pressure by placement of a second device in the bone remote from the first location.

Figure 9:
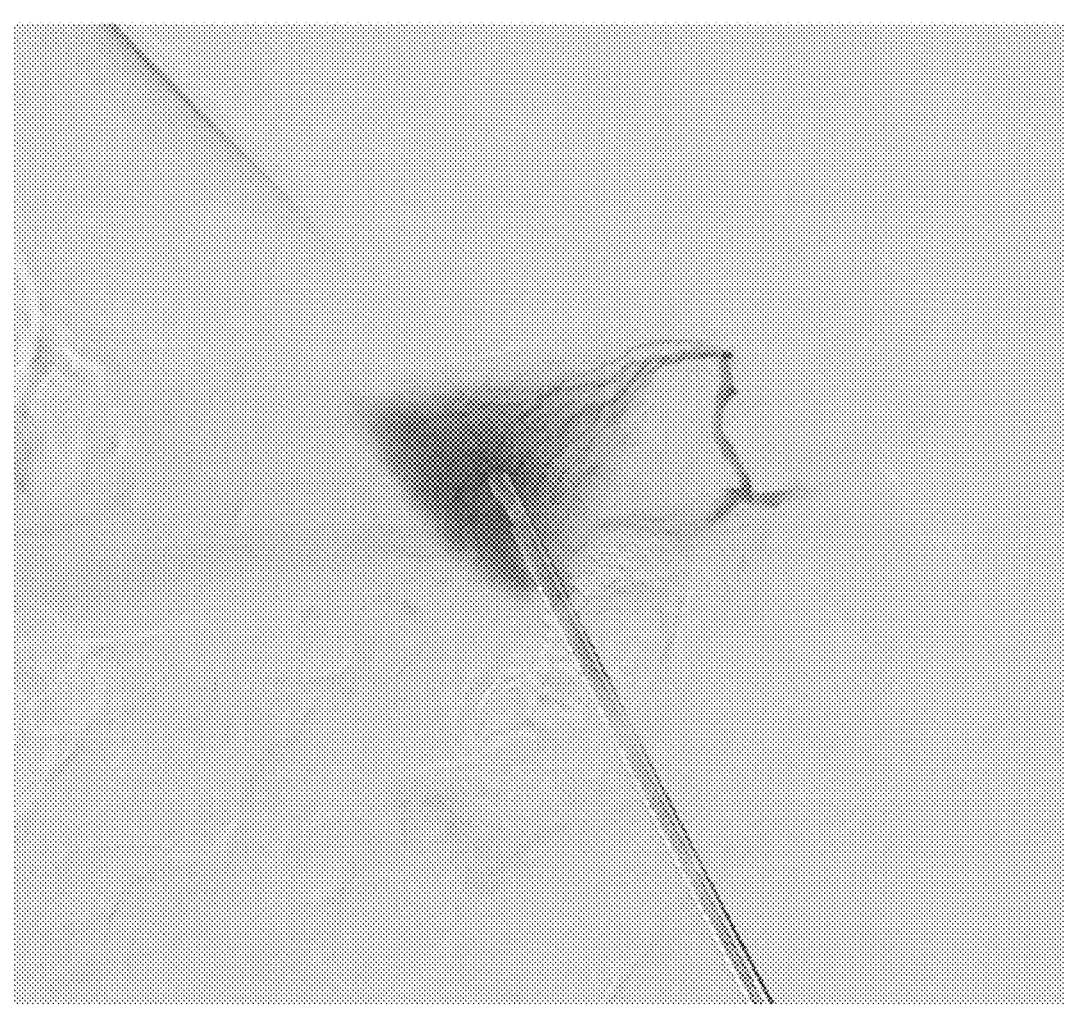
FIG. 9 is a fluoroscopic image of a contrast dye administrated with epinephrine into a subject's bone at a rate of 5 mL/second maximum distribution. Of note are the constricted intraosseous draining venules and veins. Note the comparatively small bone perfusion field due to placement of the administration needle in close proximity to a draining central vein.

FIG. 9 is a fluoroscopic image of a contrast dye administrated with epinephrine into a subject's bone at a rate of 5 mL/second maximum distribution. Of note are the constricted intraosseous draining veins as well as a relatively small bone perfusion field due to close proximity to a draining central vein.

Figure 10:
FIG. 10 is a fluoroscopic image of a contrast dye administrated without epinephrine into a subject's bone at a rate of 5 mL/second maximum distribution. The injection site distance is maximized from a draining central vein. Of note is the much larger field of drug opacification.

FIG. 10 is a fluoroscopic image of a contrast dye administrated without epinephrine into a subject's bone at a rate of 5 mL/second maximum distribution. The injection site distance is maximized from a draining central vein. Of note is the much larger field of drug opacification.

Figure 11:
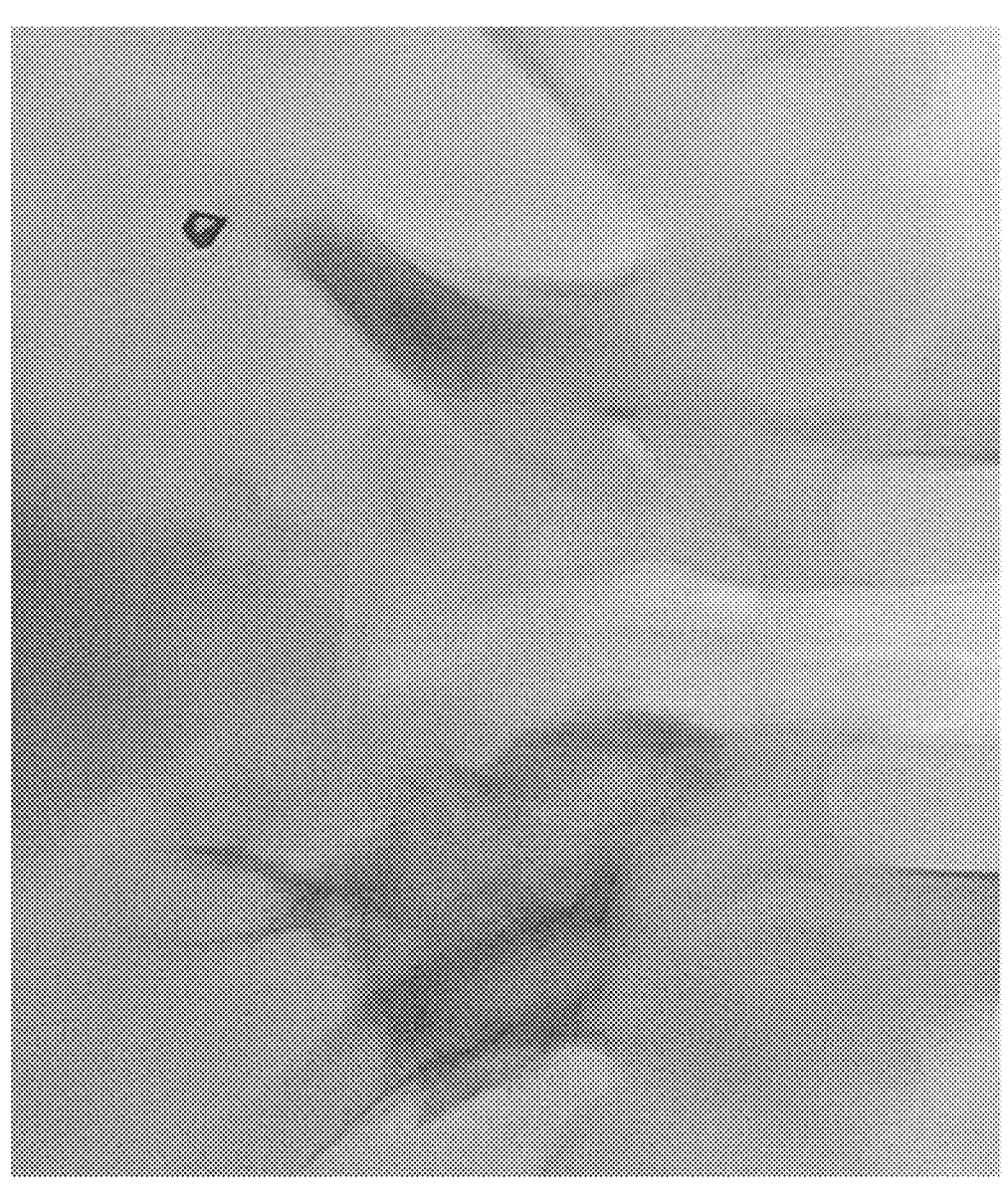
FIG. 11 is a fluoroscopic image of a contrast dye administrated with epinephrine into a subject's bone at a rate of 5 mL/second maximum distribution. The injection site distance is maximized from a draining central vein. The rate of contrast clearance is decreased, though the field of opacification is not as large, possibly due to constricted venules.

FIG. 11 is a fluoroscopic image of a contrast dye administrated with epinephrine into a subject's bone at a rate of 5 mL/second maximum distribution. The injection site distance is maximized from a draining central vein. The rate of contrast clearance is decreased and the field of opacification increased compared to placement of the device close to the draining vein. However, the field of opacification is not as large compared to the injection before epinephrine injection, possibly due to constricted venules limiting lateral flow within the bone. This may be obviated by a second device in a different location or by administration of the vasoconstricting agent to a site in close proximity to the draining vein of bone.

Figure 12:
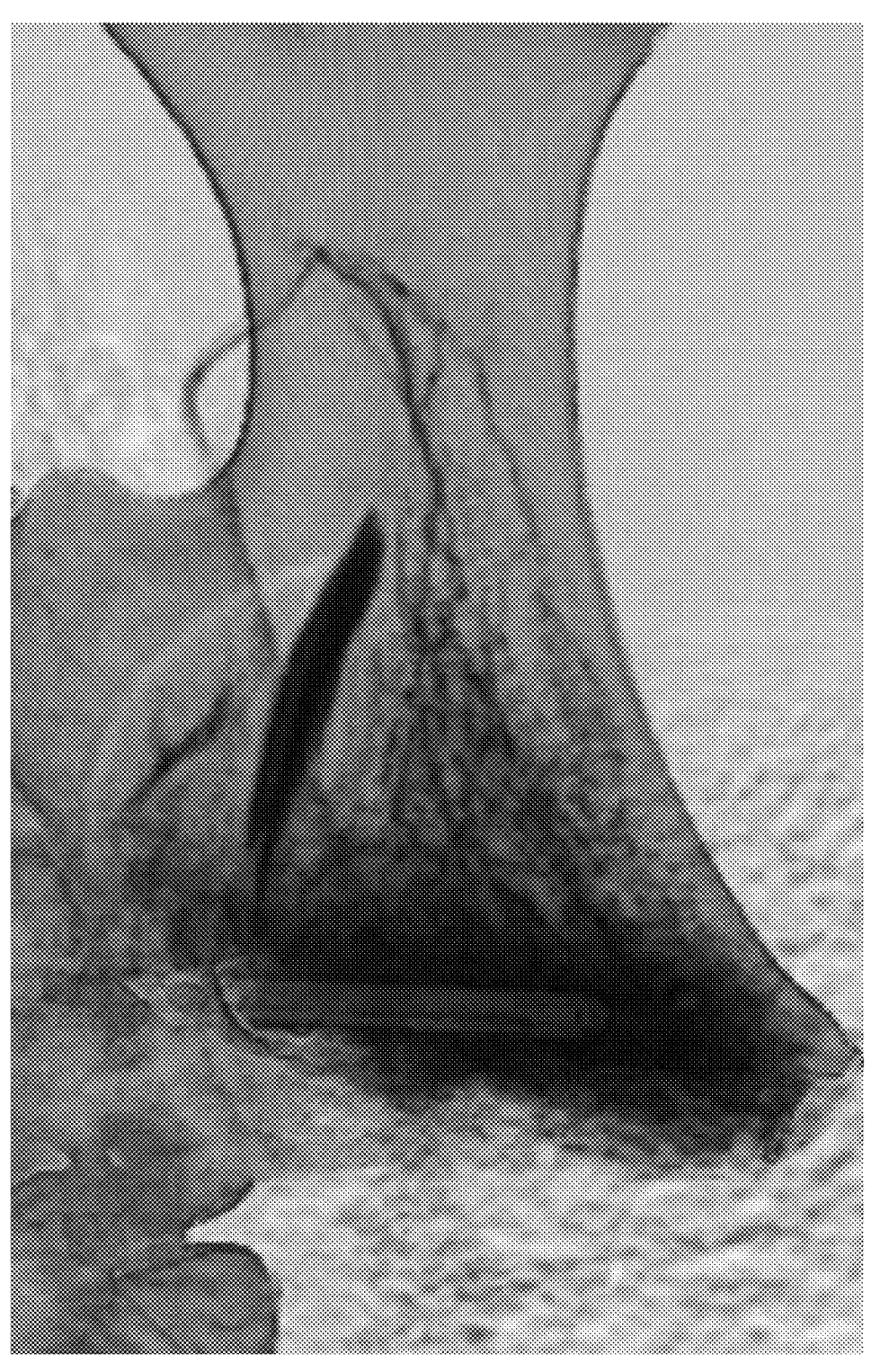
FIG. 12 is a fluoroscopic image of a contrast dye administrated with epinephrine into a subject's bone at a rate of 5 mL/second maximum distribution 20 minutes after injection. The contrast dye with epinephrine remains in the bone at 20 minutes despite the smaller perfusion field.

FIG. 12 is a fluoroscopic image of a contrast dye administrated with epinephrine into a subject's LEFT bone at a rate of 5 mL/second maximum distribution 20 minutes after injection. The contrast dye with epinephrine remains in the bone despite the smaller perfusion field.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of modulating a rate of egress and intraosseous distribution of a first injectate, comprising steps of:
   providing a volume of the first injectate comprising at least one therapeutic agent;
   injecting the volume of the first injectate into a first region of an intramedullary bone site;
   providing a volume of a second injectate comprising at least one vasoactive agent;

injecting the volume of the second injectate into a second region of the intramedullary bone site, wherein the first and second regions are different regions; and maintaining the volume of the first injectate within the intramedullary bone site in a localized state such that between 15% to 95% of the volume of the first injectate is retained for between 5 minutes to 2 hours.

2. The method of claim 1, wherein the step of providing the volume of the first injectate is preceded by a step of providing a volume of a preliminary injectate at a pressure selected from the group consisting of about: 10 psi, 20 psi, 30 psi, 40 psi, 50 psi, 60 psi, 70 psi, 80 psi, 90 psi, 100 psi, 200 psi, 300 psi, 400 psi, 500 psi, 600 psi, 700 psi, 800 psi, 900 psi, and 1000 psi, wherein connections between surrounding venules at the intramedullary bone site are opened by way of incomplete or fragile sinusoidal walls.

3. The method of claim 1, wherein the step of providing the volume of the first injectate is preceded by a step of providing a volume of a preliminary injectate at a rate-selected from the group consisting of about: 0.1 µL/s, 1 µL/s, 10 µL/s, 50 µL/s, 0.1 mL/s, 0.2 mL/s, 0.3 mL/s, 0.4 mL/s, 0.5 mL/s, 0.6 mL/s, 0.7 mL/s, 0.8 mL/s, 0.9 mL/s, 1 mL/s, 2 mL/s, 3 mL/s, 4 mL/s, 5 mL/s, 6 mL/s, 7 mL/s, 8 mL/s, 9 mL/s, and 10 mL/s, wherein connections between surrounding venules at the intramedullary bone site are opened by way of incomplete or fragile sinusoidal walls.

4. The method of claim 1, wherein the at least one vasoactive agent is a vasoconstrictive agent selected from the group consisting of: a sympathomimetic, methoxamine hydrochloride, epinephrine, dobutamine, dopamine, norepinephrine, milrinone, midodrine hydrochloride, desglymidodrine, and an alphareceptor agonist, stimulant or activator.

5. The method of claim 1, wherein the at least one vasoactive agent is a vasodilative agent selected from the group consisting of: alpha or beta adrenergic receptor modulators, muscarine, histamine, dopamine receptor modulators, an organic nitrate, isosorbide mononitrate, a mononitrate, isosorbide dinitrate, a dinitrate, nitroglycerin, a trinitrate, minoxidil, sodium nitroprusside, hydralazine hydrochloride, nitric oxide, nicardipine hydrochloride, fenoldopam mesylate, diazoxide, enalaprilat, epoprostenol sodium, a prostaglandin, milrinone lactate, a bipyridine, and a dopamine D1-like receptor agonist, stimulant or activator.

6. The method of claim 1, wherein the at least one therapeutic agent is selected from the group consisting of: an anti-tumor agent, an antiproliferative agent, an anti-angiogenic agent, a cytotoxic agent, an antimicrobial (including anti-bacterial and anti-fungal) agent, a cell mobilizing agent, and a pain-relieving agent.

7. The method of claim 1, further comprising a step of extracting a volume of aspirate from one or more additional regions of the intramedullary bone site after the step of maintaining the volume of the first injectate within the intramedullary bone site in the localized state, such that a pressure gradient is formed across a vasculature or a bone field between the intramedullary bone site having a first pressure and the one or more additional regions of the intramedullary bone site each having a pressure lower than the first pressure.

8. The method of claim 7, wherein the one or more additional regions of the intramedullary bone site are each between about 5 mm to about 500 mm distant from the first region of the intramedullary bone site.

9. The method of claim 7, wherein the step of injecting the volume of the first injectate and the step of extracting are performed at sequential depths at the first region of the intramedullary bone site and the one or more additional regions of the intramedullary bone site, respectively.

* * * * *